United States Patent
Seidel et al.

(10) Patent No.: US 10,585,274 B2
(45) Date of Patent: Mar. 10, 2020

(54) METHOD FOR CAPTURING AND COMPENSATING AMBIENT EFFECTS IN A MEASURING MICROSCOPE

(71) Applicant: Carl Zeiss SMT GmbH, Oberkochen (DE)

(72) Inventors: Dirk Seidel, Jena-Leutra (DE); Carola Blaesing-Bangert, Rothenstein (DE); Oliver Jaeckel, Jena (DE)

(73) Assignee: Carl Zeiss SMT GmbH, Oberkochen (DE)

( * ) Notice: Subject to any disclaimer, the term of this patent is extended or adjusted under 35 U.S.C. 154(b) by 0 days.

(21) Appl. No.: 16/026,364

(22) Filed: Jul. 3, 2018

(65) Prior Publication Data

US 2019/0011690 A1 Jan. 10, 2019

(30) Foreign Application Priority Data

Jul. 10, 2017 (DE) .................. 10 2017 115 367

(51) Int. Cl.
*G02B 21/36* (2006.01)
*G01N 21/45* (2006.01)
(Continued)

(52) U.S. Cl.
CPC .......... *G02B 21/367* (2013.01); *G01B 11/026* (2013.01); *G01B 11/03* (2013.01);
(Continued)

(58) Field of Classification Search
CPC .... G02B 21/367; G01B 11/026; G01B 11/03; G01N 21/45
See application file for complete search history.

(56) References Cited

U.S. PATENT DOCUMENTS 6,884,992 B1 4/2005 Heiland
7,450,246 B2 11/2008 Boesser et al.
(Continued)

FOREIGN PATENT DOCUMENTS

DE 197 18 799 11/1998 ............ H01J 37/28
DE 102005035700 11/2006 ............ G01B 11/02
(Continued)

OTHER PUBLICATIONS

German Patent Office Examination Report for German Application No. DE 10 2017 115 367.5 dated Mar. 7, 2018.

*Primary Examiner* — Jamie J Atala
*Assistant Examiner* — Michael Robert Cammarata
(74) *Attorney, Agent, or Firm* — Fish & Richardson P.C.

(57) ABSTRACT

The invention relates to a method for capturing and compensating the influence of ambient conditions on an imaging scale (S) in a measuring microscope. Here, a modification of the optical properties in the measuring microscope that is caused by a change in the ambient conditions is measured by use of a reference measurement system, in particular an etalon, and, at the same time, an image of a reference structure with at least one reference length (L0) that is situated on a calibration mask is produced by use of a detector of the measuring microscope and a change (ΔL) of the reference length (L0) that is caused by the change in the ambient conditions is determined in the image of the reference structure. Subsequently, a correlation is established between the modification of the optical properties of the reference measurement system and the length change (ΔL) in the image, produced in the detector, of the reference structure of the calibration mask. This correlation can be used to carry out a computational adaptation of the size of picture elements of the detector and thus compensate the (Continued)

influence of ambient conditions on the imaging scale (S) of the measuring microscope.

22 Claims, 6 Drawing Sheets

(51) Int. Cl.
    *G01B 11/02*     (2006.01)
    *G01B 11/03*     (2006.01)
    *G03F 1/84*     (2012.01)
    *G01B 21/04*     (2006.01)
    *G02B 21/00*     (2006.01)
    *G01M 11/02*     (2006.01)
    *G02B 27/62*     (2006.01)

(52) U.S. Cl.
    CPC ....... *G01B 21/045* (2013.01); *G01M 11/0264* (2013.01); *G01M 11/0271* (2013.01); *G01N 21/45* (2013.01); *G02B 21/0016* (2013.01); *G03F 1/84* (2013.01); *G01N 2021/458* (2013.01); *G02B 27/62* (2013.01)

(56) References Cited

U.S. PATENT DOCUMENTS

| | | | |
|---|---|---|---|
| 9,528,825 B2* | 12/2016 | Blaesing-Bangert | ........................ G01B 21/16 |
| 2007/0103667 A1 | 5/2007 | Ferber et al. | |
| 2007/0268496 A1* | 11/2007 | Boesser | .............. G03F 7/70775 356/508 |
| 2008/0201971 A1 | 8/2008 | Heiden et al. | |
| 2012/0160007 A1 | 6/2012 | Kerwien et al. | |
| 2012/0327209 A1* | 12/2012 | Folling | .................. G02B 21/16 348/79 |
| 2014/0307949 A1 | 10/2014 | Eyring et al. | |
| 2017/0269347 A1 | 9/2017 | Jaeckel et al. | |

FOREIGN PATENT DOCUMENTS

| | | | | |
|---|---|---|---|---|
| DE | 102005052758 | | 5/2007 | ............. G01B 11/00 |
| DE | 102009019140 | | 11/2010 | ............... G03F 9/00 |
| DE | 102016204535 | | 9/2017 | ............... G01B 9/04 |

* cited by examiner

METHOD FOR CAPTURING AND COMPENSATING AMBIENT EFFECTS IN A MEASURING MICROSCOPE

CROSS REFERENCE TO RELATED APPLICATIONS

This application claims priority under 35 U.S.C. § 119 from German Application DE 10 2017 115 367.5, filed on Jul. 10, 2017, the entire content of which is incorporated herein by reference in its entirety.

TECHNICAL FIELD

The invention relates to capturing and compensating ambient effects in a measuring microscope. In particular, the invention relates to a method for capturing the influence of ambient conditions on an imaging scale in a measuring microscope, as is used for measuring masks or wafers for photolithography systems, for example. Such measuring microscopes are often used as part of a so-called mask inspection system or wafer inspection system.

BACKGROUND

In lithographic methods for producing microstructured or nanostructured components for microelectronics or microsystem engineering, structures on a mask, a so-called reticle, are imaged on a semiconductor material in order thus to produce conductor tracks and semiconductor components. In order to be able to produce structures in the nanometer range on the semiconductor material, the structures have to be produced and positioned highly precisely on the reticle. In order to monitor the quality and measure the dimensional accuracy of the structures on the reticle, use is made of measurement methods and measuring microscopes, as are described in DE102009019140A1 and US 2014/0307949A1, for example.

Establishing the position of the masks is based upon an interferometric length measurement. To this end, special adjustment marks on a mask are captured in respect of the position thereof by use of a microscopic image. The individual adjustment marks or structure elements of the mask are successively driven into the center of the image field by way of a positioning stage and the position of the respective adjustment marks is established. Thereupon, the distance from the adjustment mark measured previously is established by determining the path traveled by the positioning stage between the measurements. The path traveled by the positioning stage is established by use of an interferometric measurement.

In order to facilitate highly accurate measurements of the reticles, it is necessary to very precisely know and optionally compensate the influence of variations in the ambient conditions (e.g., temperature, air pressure, humidity, . . . ) on the mask to be measured and on the measuring microscope used to carry out this measurement. A (natural or artificially produced) change in these ambient conditions leads to a change in the optical medium within an imaging optical unit of the measuring microscope which, in general, consists of a multiplicity of lens elements with air interstices. These interstices may also be purged with nitrogen. Furthermore, the mechanical hold of the lens elements may depend on ambient conditions such as air pressure and air temperature, for example. Consequently, the scale ratios of the projection exposure apparatus change in the case of a temporal modification of the ambient conditions. A typical change in the optical path in a measuring microscope on account of air pressure variation lies at 20 nm/mbar. Such a change appears to be relatively small, but it is very important for highly accurate measuring appliances, as are used, for example, for measuring photolithographic masks with structures in the nanometer range.

It is known that variations in the ambient conditions cause changes in the focal position in the measuring microscope. This effect is relevant, in particular, if the measuring microscope uses the focus position, for example to carry out a height measurement of a reticle for photolithographic applications. A method for establishing and compensating this effect is described in (file reference DE 10 2016 204 535), for example.

Furthermore, changes in the ambient conditions have an influence on the magnification of the optical imaging in the measuring microscope. As a consequence, the distances between two structures to be measured change in the image field of the measuring microscope when the ambient conditions vary. Such variations typically are of the order of up to 1.5-2 ppm; they therefore represent a noticeable effect, which leads to falsifications of the measurement results, for highly accurate measuring appliances, as are used, for example, for measuring structures on reticles. Until now, a satisfactory solution for compensating this effect had not been known.

SUMMARY

In a general aspect, the present invention specifies a method, by use of which the influence of changes in the ambient conditions (e.g., temperature, air pressure, humidity, air gas composition, . . . ) on the scale ratios in a measuring microscope can be established and compensated.

In another general aspect, a method for capturing the influence of ambient conditions on an imaging scale in a measuring microscope of a mask inspection system or a wafer inspection system is provided. A modification of the optical properties in the measuring microscope that is caused by a change in the ambient conditions is measured by use of a reference measurement system, and an image of a reference structure with at least one reference length that is situated on a calibration mask is produced by use of a detector of the measuring microscope. A change in the reference length that is caused by the change in the ambient conditions is determined in the image of the reference structure. A correlation is established between the modification of the optical properties of the reference measurement system and the length change in the image, produced in the detector, of the reference structure of the calibration mask.

Implementations of the method can include the following feature. The deviation of an optical path from a reference value that is caused by changes in the ambient conditions can be established in the reference measurement system.

A method according to the invention proceeds from a measuring microscope in a mask inspection system or wafer inspection system, which comprises a detector for producing a digital image of an object to be measured, for example a calibration mask with a reference structure, that is situated in the visual field of the measuring microscope. Furthermore, provision is made of a reference measurement system, with the aid of which a modification of optical properties, in particular a change in the refractive index and/or a change in the number of wavelengths and an interferometer, that is caused by a change in the ambient conditions can be measured.

The method for capturing the inference of ambient conditions on an imaging scale of the measuring microscope provides for, firstly, a modification of the optical properties in the measuring microscope that is caused by a change in the ambient conditions to be measured by use of the reference measurement system and, secondly, a length change of the reference structure that is caused by the change in the ambient conditions to be determined in the image of the detector of the measuring microscope. Subsequently, a correlation is established between the change in the optical properties of the reference measurement system and the length change of the reference structure. This correlation provides information about how the size ratios of the structures that are imaged in the detector of the measuring microscope change when changes in the ambient parameters (and hence changes in the optical properties) occur and forms the basis for a compensation of the changes in the imaging scale of the measuring microscope caused by ambient effects. This method can be applied not only to measuring microscopes but also to optical measurement systems in the most general sense.

By way of example, changes in the refractive index of the optical medium (e.g., air) present in the measuring microscope or changes in an optical path can be established in the reference measurement system, which serves to establish the modification of the optical properties in the measuring microscope that is caused by changes in the ambient conditions. In particular, an etalon which is integrated in the measuring microscope, which comprises an interferometer and the mirror and which facilitates a highly precise measurement of changes in the optical path (by measuring the change in the phase of laser light) is particularly suitable as a reference measurement system.

Advantageously, the calibration mask has a reference structure with a periodic grid. A multiplicity of reference coordinate values and the length changes thereof are established in order to ensure a high measurement accuracy when establishing the reference length or length changes. Furthermore, it may be advantageous to displace different portions of the reference structure into the image field of the detector and measure said portions, and subsequently carry out averaging over the measurement data obtained in the process.

After a reference value of the length scale was established at a reference time, measurements are now carried out at temporal intervals, at which the current value of the length scale and the change in the refractive index or the optical path in relation to the value of the reference time are established simultaneously. Changes in the ambient conditions influence the length scale and the refractive index of the optical path, and so a plurality of measurement data pairs are obtained when carrying out a plurality of measurements at different ambient conditions. A graphical evaluation of the relative change in the length scale as a function of the change in the refractive index or the change in the optical path shows that an approximately linear correlation is present between these two measurement data. From this, it is possible to derive a (constant) correction value for the imaging scale of the measuring microscope, said correction value specifying the extent to which length scales are modified in the image of the measuring microscope under the influence of changes in the ambient conditions. Now, this correction value can be used to adapt the size of picture elements in the detector by computation in such a way that the influence of changing ambient conditions on the imaging scale of the measuring microscope (and consequently on length measurements in the measuring microscope) are largely compensated.

In the cases in which a global correction value (i.e., a correction value that is uniform over the whole area) does not suffice to describe the influence of the changes in the ambient conditions on the entire object to be measured, it is possible to establish local correction values, with the aid of which a distortion function is calculated, said distortion function taking account of the (local) ambient effects correctly over the image field. In particular, this correction function can be represented as a function of a complete basis of 2D vector functions.

BRIEF DESCRIPTION OF DRAWINGS

Exemplary embodiments and variants of the invention will be explained in more detail below with reference to the drawing. In the figures.

DETAILED DESCRIPTION

Figure 1:
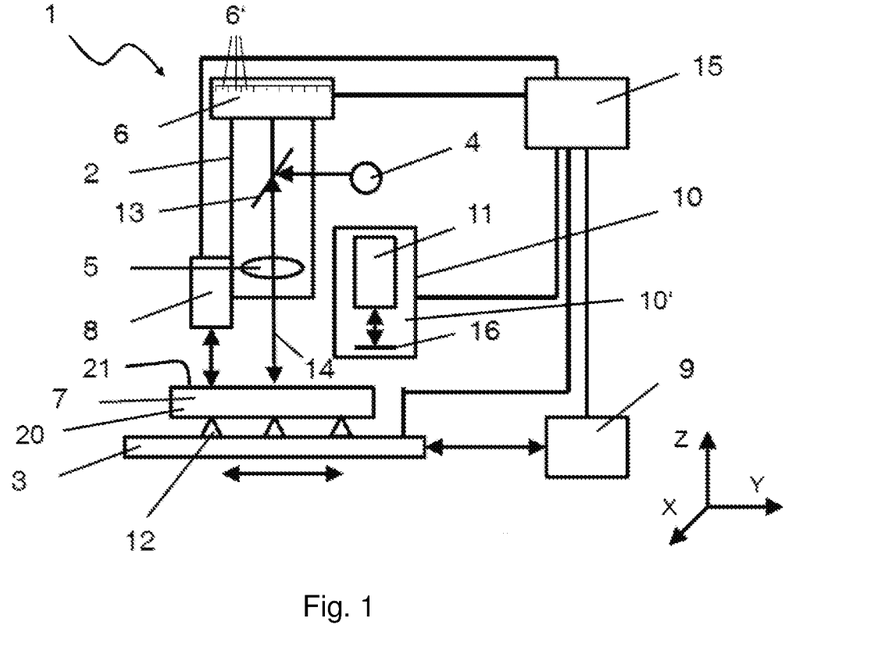
FIG. 1 shows an illustration of a measuring microscope according to the present invention.
Figure 2:
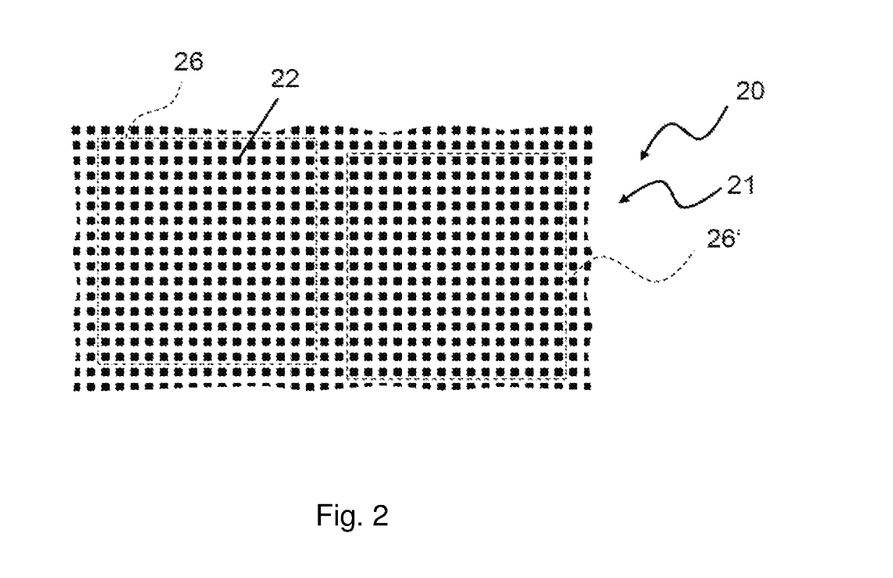
FIG. 2 shows a plan view of a portion of a calibration mask with a reference structure.

FIG. 1 shows a schematic illustration of a measuring microscope 1 for measuring structured elements, for example reticles for use in lithographic apparatuses. The measuring microscope 1 comprises a microscope body 2, in which a measuring objective 5 is arranged. Furthermore, the measuring microscope 1 comprises a light source 4, with which it is possible to illuminate a structured element 7, for example a reticle with a structure to be examined, that is arranged on a displaceable platform 3 (a so-called "stage"). In particular, a calibration mask 20 with a reference structure 21 can be used as a structured element 7; FIG. 2 shows a plan view of a portion of such a calibration mask 20.

The light source 4 radiates illumination light 14 onto the calibration mask 20 via a beam splitter 13 in the microscope body 2, wherein the illumination light 14 that is reflected by the calibration mask 20 is imaged on the detector 6 such that an image of the calibration mask with reflected-light illumination can be captured in the detector 6. Likewise, in another embodiment, the light transmitted by the calibration mask 20 can be imaged on the detector 6 using transmitted-light illumination. By way of example, the detector 6 can be a CCD camera.

The stage 3 is movable in three independent spatial directions and the calibration mask 20 is mounted on the stage 3 by use of a three-point bearing 12, with the calibration mask 20 preferably resting on hemispherical elements. Alternatively, the calibration mask 20 can also rest on the mask holder by use of the three-point bearing, said mask holder resting on the stage 3. The stage 3 can be moved in an XY-plane perpendicular to the direction of the optical axis of the measuring microscope 1 (corresponding to the direction of the illumination light beam 14, which is denoted by Z in FIG. 1). Accordingly, the calibration mask 20 can be moved on the stage in two independent spatial directions, in the X-direction and Y-direction corresponding to the Cartesian coordinate system.

At least two interferometers 9 are used to establish the spatial position of the stage 3 and the XY-plane, only one of said interferometers, which serves to measure displacements of the stage in the X-direction, being illustrated in FIG. 1. At least one further interferometer 8 is provided for establishing the position of the stage 3 in the Z-direction. The various measuring devices, such as, e.g., the detector 6, the device 10 for establishing the refractive index, the interferometers 8, 9 and/or devices with drives and/or actuators, such as the stage 3, are connected to a control and regulating device 15 comprising an evaluation unit, and so desired information items may be established from the established measurement data and at least parts of the measuring microscope 1 may be controlled accordingly on the basis of these information items.

Furthermore, the measuring microscope 1 has a reference measurement system 10, by use of which it is possible to measure modifications of the optical properties of the medium present in the measuring microscope 1, e.g., air, that are caused by a change in the ambient conditions. The reference measurement system 10 is situated in the immediate vicinity of the microscope body 2 in order to capture variations in the ambient conditions, which act on the optical unit of the measuring microscope 1, as exactly as possible. The reference measurement system can contain conventional sensors for air pressure p, air temperature T, and humidity F, etc. From the measurement values of these sensors, it is possible to establish the ambient refractive index n (p, T, F) by use of the following formula (the so-called Edlen formula):

$$n(p, T, F) = \qquad (1)$$
$$1 + (3.83639 \times 10^{-7} \times p) \left[ \frac{1 + p \times (0.817 - 0.0133 \times T) \times 10^{-6}}{1 + 0.003661 \times T} \right] -$$
$$5.607943 \times 10^{-7} \times F$$

It should be noted here that the air pressure is the dominant variable in this formula in view of the ambient variations to be expected.

Even though formula (1) allows the refractive index n(P, T, F) to be established in general, the sensitivity of commercially available sensors generally does not suffice to measure effects in the relevant order of magnitude. Therefore, an etalon 10' is used as a reference measurement system 10 in the present exemplary embodiment. Such an etalon 10' comprises an interferometer 11 and a mirror 16, which are situated together and at a fixed distance from one another in a thermally highly stable housing. An optical path W between the interferometer 11 and the mirror 16 can be measured with great accuracy with the aid of the etalon 10'. Changes in the ambient conditions (for example, as a result of air-pressure changes or temperature variations), which accompany a change $\Delta n$ of the refractive index n of the medium (e.g., air) contained in the etalon 10', lead to a change $\Delta W$ in the optical path W in the etalon 10', wherein the measured optical path length change $\Delta W$ is directly proportional to the corresponding change $\Delta n$ in the refractive index n: $\Delta W = \Delta n \times L$, where L is the length of the etalon 10'. Consequently, a change $\Delta n$ in the refractive index can be deduced directly from a measurement of the optical path length change $\Delta W$ in the etalon 10'.

The detector 6 of the measuring microscope 1 serves to record images of the structured element 7 that is borne on the stage 3, in particular of the calibration mask 20. The detector 6 is typically a CCD camera having a multiplicity of pixels 6', which are indicated schematically in FIG. 1. An image 25, recorded by the detector 6, of a portion 26 of the reference structure 21 of the calibration mask 20, which is marked by dashed lines in FIG. 2, is displayed in FIG. 3A. The reference structure 21 of the calibration mask 20 has an orthogonal grid of equidistant markers 22, which have the form of small squares in the present exemplary embodiment. In the most general sense, it is advantageous to provide a multiplicity of marks 22 that form a regular grid of crosses, contact holes, squares, etc. However, in principle, it is sufficient if the reference structure 21 of the calibration mask allows the reproducible definition of at least one distance in the X-direction and one distance in the Y-direction of the image field.

Figure 3A:
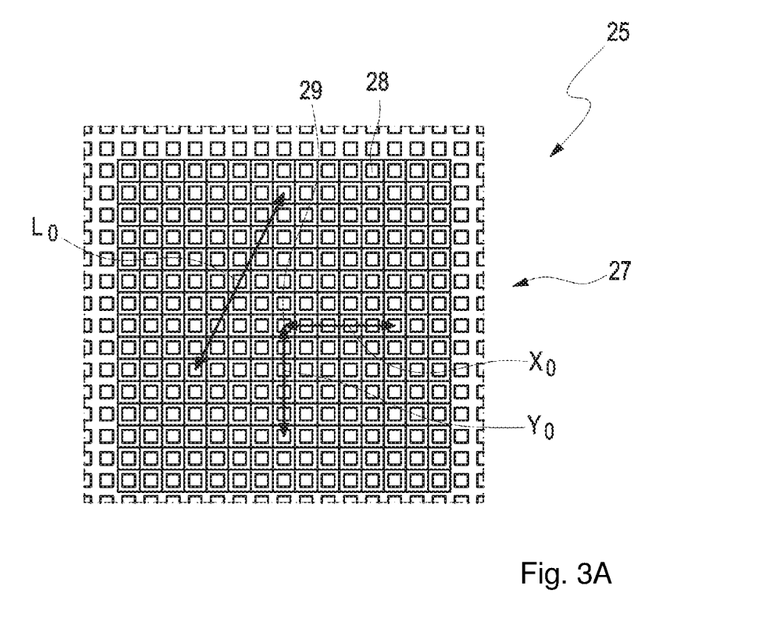
FIG. 3A shows an illustration of an image, recorded by a detector of the measuring microscope, of a portion of the calibration mask of FIG. 2 at a time t0.

The image 25 of a portion 26 of the reference structure 21, shown in FIG. 3A, shows a grid structure 27 with marks 28, which corresponds to the reference structure 21 of the calibration mask 20, but is illustrated in a magnified manner with a magnification factor (imaging scale S) of the measuring microscope 1. The portion 26 comprises 15×15 marks 28 and has an edge length $B_0$. This grid structure 27 is used to establish the influence of changing ambient conditions on the imaging scale of the measuring microscope 1.

To this end, a reference measurement is initially carried out (at the time denoted by $t_0$ below). The refractive index n has a reference value that is denoted by $n_0$ at this time $t_0$; however, the absolute value of said refractive index is irrelevant here since only deviations $\Delta n$ of the refractive index from this reference value $n_0$ are measured and used in the method described below. Furthermore, an image 25 of the portion 26 of the reference structure 21 of the calibration mask 20 is recorded at the time $t_0$ of the reference measurement. At least one reference length $L_0$ is established from this image 25.

It should be noted here that the calibration mask 20 was typically produced in the same manner as conventional masks 7 by use of an electron beam writer. The dimensional errors or inaccuracies at the resultant reference structure 21 arising on account of this manner of production are recognizable in FIG. 3 and are so large that the desired accuracy in the measuring microscope 1 cannot be achieved in the case of a direct calibration using this calibration mask 20. Therefore, it is advantageous to determine a multiplicity of reference coordinate values $X_0(m)$ with $m=1, \ldots m_{Max}$ and $Y_0(m)$ with $m=1, \ldots m_{Max}$ in order to average out possibly present inaccuracies in the reference structure 21. In the present exemplary embodiment of FIG. 3A, a multiplicity of reference coordinate values $X_0$, $Y_0$ of a number of a total $m_{Max}$ of markings 28 was determined in the coordinate system of the grid structure 27 with the coordinate origin 29; specifically, the coordinate values $X_0$, $Y_0$ were established on a grid of 15×15 marks 28.

Furthermore, it is advantageous to measure a plurality of different portions 26, 26' of the reference structure 21 (see FIG. 2a); this can be achieved by displacing the calibration mask 20 in the X-direction and Y-direction with the aid of the stage 3. Alternatively, or additionally, the calibration mask 20 can be rotated through an angle of 90° about the Z-axis between the measurements for the purposes of achieving different measurement positions. Overall, $s_{Max}$ images of the reference structure 21 are recorded in different portions or orientations, from which the reference coordinate values $X_0(m,s)$ and $Y_0(m,s)$ with $m=1, \ldots m_{Max}$ and $s=1, \ldots s_{Max}$ are then calculated. Consequently, $m_{Max} \times s_{Max}$ measurement values are obtained for the reference distance $L_0$. Here, it can be advantageous to average over the distance values recorded in different portions orientations:

$$X_0(m) = \sum_{s=1}^{s_{Max}} X_0(m, s) \quad Y_0(m) = \sum_{s=1}^{s_{Max}} Y_0(m, s) \quad (2)$$

Figure 3B:
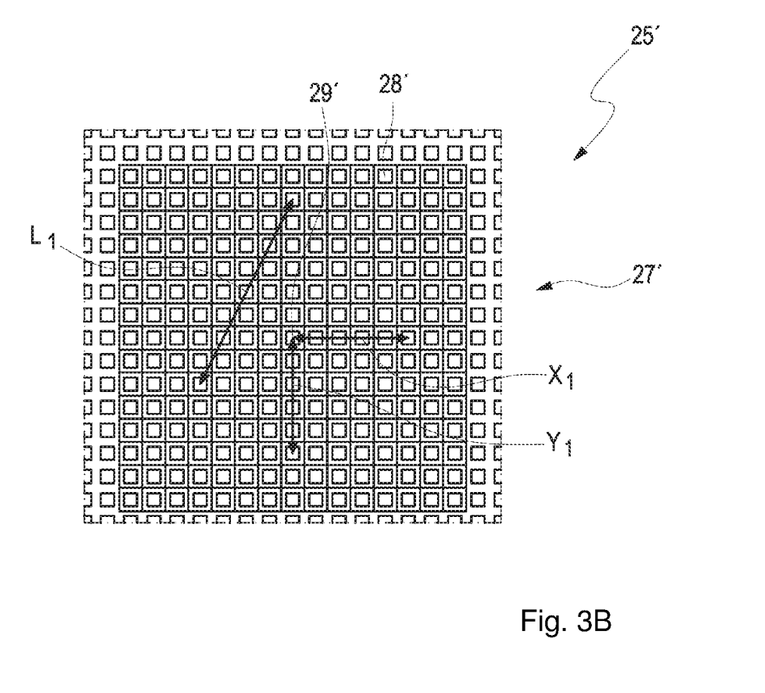
FIG. 3B shows the image portion of FIG. 2 at a time t1>t0.

Once this reference measurement has been completed, a further image 25' is recorded in a manner analogous to the method described above at a later time $t_1 > t_0$ in order to ascertain the positions of the marks 22 of the reference structure 21. A change $\Delta n = (n_1 - n_0)$ in the refractive index n, which has occurred during the time span $t_1 - t_0$ on account of modified ambient conditions, is measured with the aid of the reference measurement system 10; if the etalon 10' of FIG. 1 is used as reference measurement system 10, a change $\Delta W = (W_1 - W_0)$ in the optical path in the etalon, which is directly proportional to $\Delta n$, is measured instead. The change $\Delta n$ in the refractive index n has as a consequence that the positions of the marks 28' in the image 25' of the reference structure 21 at this time $t_1$ have been displaced in relation to the original positions at the time $t_0$ and the portion 26 of the 15×15 marks in the image 25', marked in FIG. 3A, now has an edge length $B_1$, which, in the present exemplary embodiment, is greater than the edge length $B_0$ in the image 25; this is illustrated in FIG. 3B in a greatly exaggerated manner. The current values of the length scale $L_1$ or the current values of the coordinates $X_1$ (m,s) and $Y_1(m,s)$ and the relative changes $\Delta X(m,s) = (X_1(m,s) - X_0(m,s))/X_0(m,s)$ and $\Delta Y(m,s) = (Y_1(m,s) - Y_0(m,s))/Y_0(m,s)$ of these distances in relation to the reference measurement are now established from the image 25'.

These measurements can be repeated at a multiplicity of times $t_i$, $i=1, \ldots, i_{Max}$ in order to determine the associated refractive index $n_i$ and the mark positions $X_i$, $Y_i$ for a multiplicity of different ambient conditions.

Figure 4:
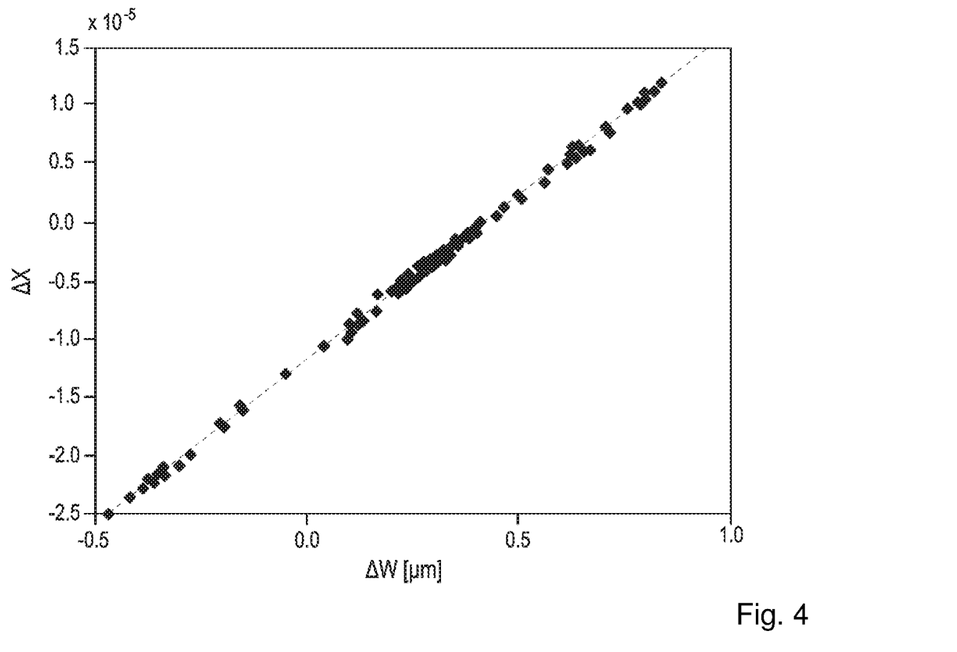
FIG. 4 shows a diagram of measurement values of relative distance changes in the detector image of FIG. 3 as a function of a change in an optical path in a reference measurement system for a multiplicity of measurements under different ambient conditions.

FIG. 4 shows a schematic illustration of the dependence of the relative distance change $\Delta X(m,s) = (X_i(m,s) - X_0(m,s))/X_0(m,s)$ as a function of the change in the optical path $\Delta W = (W_1 - W_0)$ in the etalon 10' for a multiplicity of measurements $i=1, \ldots, i_{Max}$. Here, the ambient changes led to the variation in the optical path length and the employed etalon 10' of approximately 1.3 µm, corresponding to an air pressure change of approximately 18 mbar. It is possible to recognize that, to a good approximation, there is a linear dependence between these two measurement values in the shown example, and so the imaging scale S reacts approximately proportional to the refractive index in the case of changes of the ambient conditions:

$$\Delta S = S - S_0 = (a \times \Delta n), \quad (3)$$

where $S_0$ is the imaging scale under reference ambient conditions and a is a scaling constant.

Depending on the specific configuration of the considered apparatus, for example of the measuring microscope, there may also be a nonlinear relationship between the change in the optical path in the etalon and the relative distance change. By way of example, this can be traced back to the influence of holders or housing parts, which likewise react to changing ambient conditions. In particular, such relationships could be represented by power series such as Taylor series, for example, or could be established by machine learning.

If it is not only a scale change but also a more complex distortion change in the measuring microscope that should be adapted, then it is likewise possible to apply the above-described method with the desired basis function of this distortion. In this case, local changes $\Delta L(x,y)$ of the local reference length $L_0(x,y)$ are determined at different locations x,y in the image 25 of the reference structure 21 instead of a uniform (averaged) length change $\Delta L$. Subsequently, a local correlation function is established between the modification of the optical properties of the reference measurement system 10 and the length change $\Delta L(x,y)$ in the image 25, produced in the detector 6, of the reference structure 21 of the calibration mask 20; with the aid of this correlation function, it is then possible, for example, to calculate a local change of the imaging scale $\Delta S(x,y)$—in a manner analogous to the above-described method.

Once the above-described calibration has been completed, it is possible to compensate a scale change in the measuring microscope that is caused by changes in the ambient conditions by virtue of the pixel size of the picture elements 6' of the detector 6 being adapted to this scale change by computation. All positions and the distance measured by the measuring microscope 1 are therefore established using a pixel size of the detector 6 (that is modified depending on the ambient conditions) such that the influence of ambient conditions on the measurement result is compensated. If $p_0$ denotes the pixel size of the detector 6 at a reference time, then the surroundings-dependent pixel size $p(\Delta W)$ that takes account of the surroundings-caused change in the optical path W in the etalon 10' is given by:

$$p(\Delta W) = (1 - a) \times p_0 \quad (4)$$

If this pixel size is used in all position and distance calculations in the images 25 recorded by the detector 6, then the effect of the scale change as a function of the change in ambient conditions is compensated.

Figure 5:
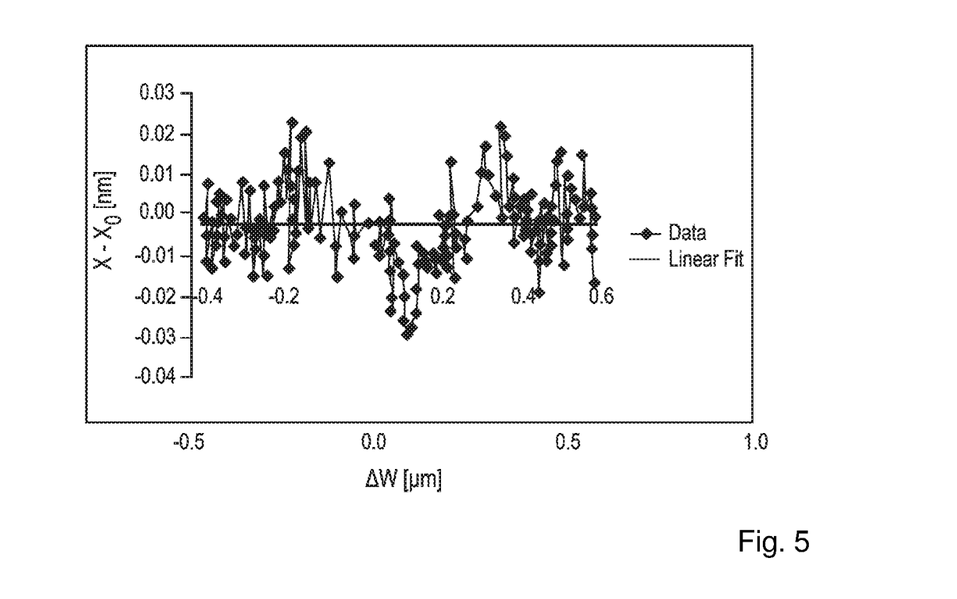
FIG. 5 shows a diagram of measurement values of absolute values of distance changes in the detector image of FIG. 3 as a function of the change in the optical path after a computational correction of the pixel size of the detector.

FIG. 5 shows the results of a measurement series, in which the formula specified at (4) was used to take account of the dependence of the refractive index on ambient conditions by correcting the pixel size. Here, the distances $\Delta X_j$ for each measurement time repetition $t_j$, $j=1, \ldots, j_{Max}$ were evaluated with a different pixel size in each case, with the instantaneous pixel size respectively given by the system-specific factor a and the averaged etalon value ΔW during this repetition; see formula (4). It is clear from FIG. 5 that the distance changes ΔX calculated in this manner are virtually constant; the distance deviations over the entire measurement time are less than 0.05 nm, with a majority of the residual error being able to be traced back to statistical noise. Consequently, the described method is well suited to compensate effects of changing ambient conditions on the imaging scale of the measuring microscope 1.

However, the method according to the invention can be used not only for adapting the sides of picture elements (pixels) by computation, but also for other adaptations, for example for adjusting the imaging scale, for correcting image positions to be measured, etc.

Figure 6:
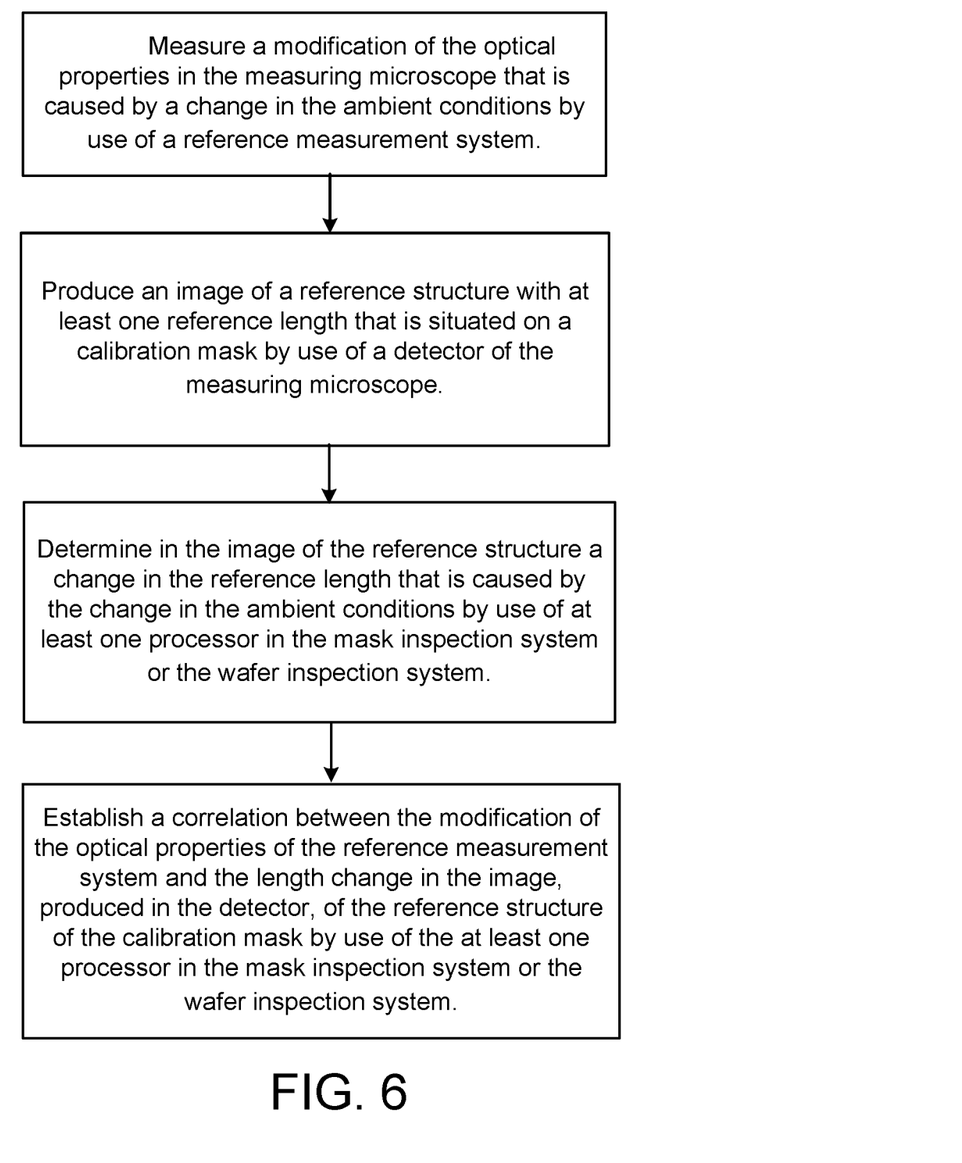
FIG. 6 shows a flow diagram of a process for capturing the influence of ambient conditions on an imaging scale in a measuring microscope of a mask inspection system or a wafer inspection system.
Figure 7:
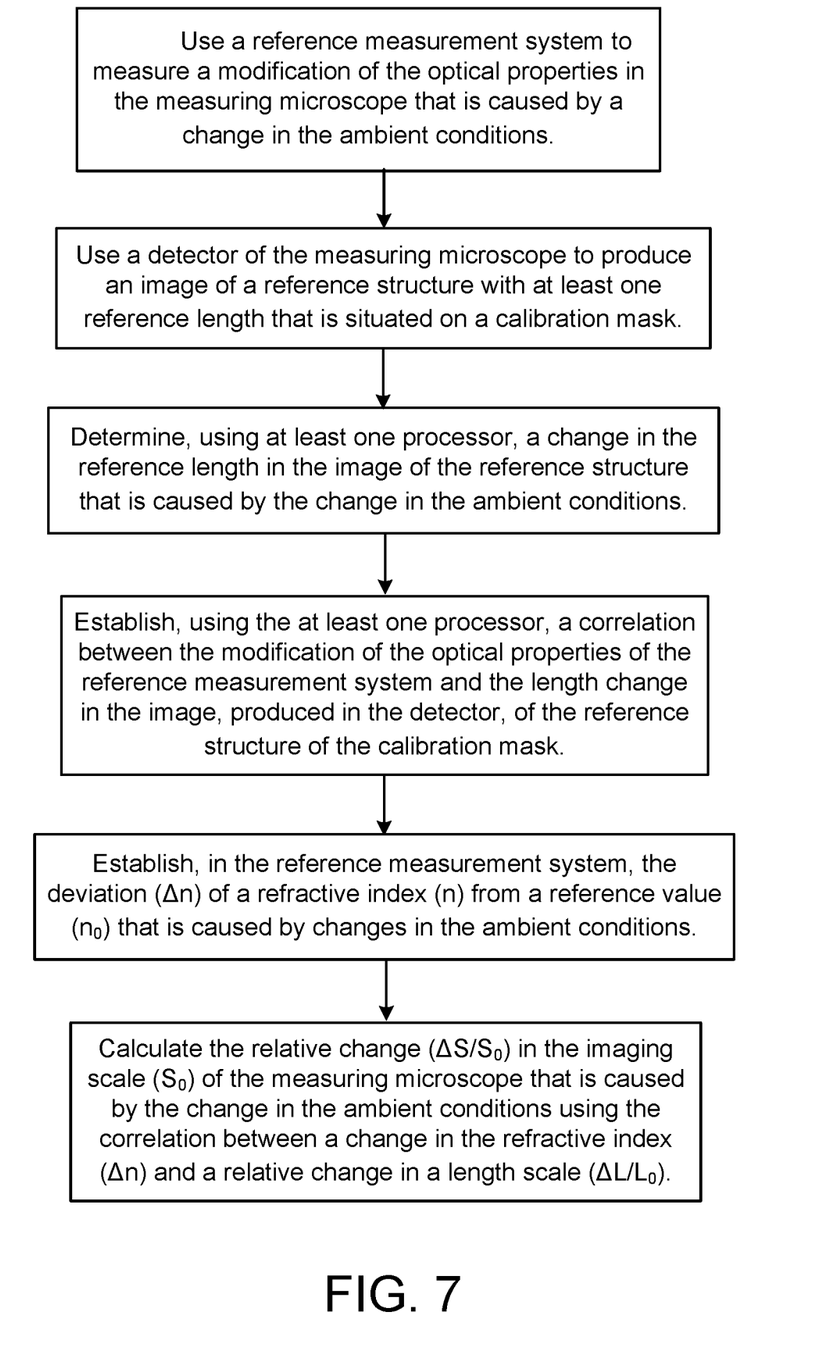
FIG. 7 shows a flow diagram of a process for calculating a relative change ($\Delta S/S_0$) in an imaging scale ($S_0$) for carrying out a computational adaptation of the size of picture elements of a detector for compensating the influence of ambient conditions on an imaging scale (S) in a measuring microscope.
Figure 8:
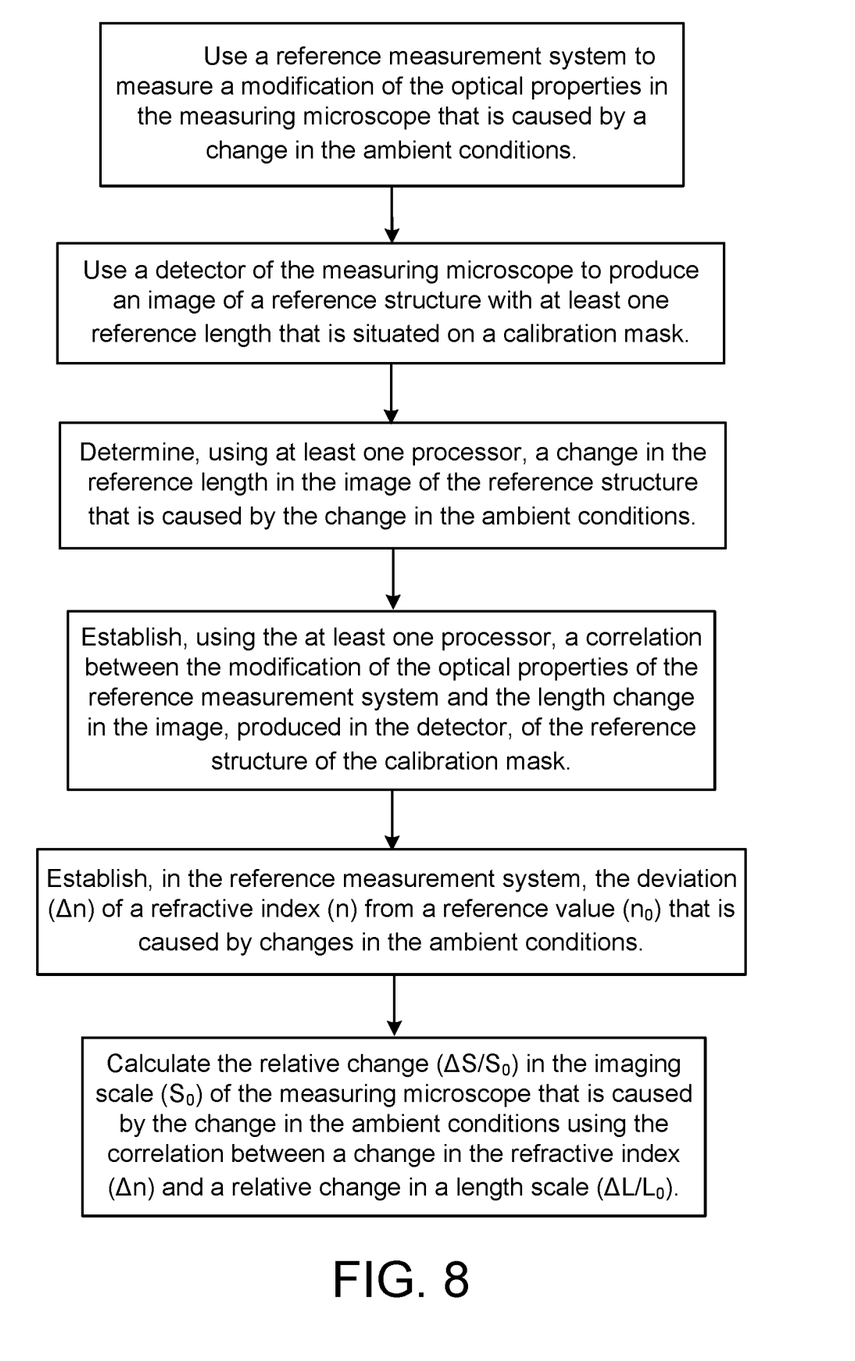
FIG. 8 shows a flow diagram of a process for calculating a relative change ($\Delta S/S_0$) in an imaging scale ($S_0$) for carrying out an adjustment of the imaging scale and/or a correction of image positions to the measured for compensating the influence of ambient conditions on an imaging scale (S) in a measuring microscope.

For example, FIG. 6 shows a flow diagram of a process for capturing the influence of ambient conditions on an imaging scale in a measuring microscope of a mask inspection system or a wafer inspection system. FIG. 7 shows a flow diagram of a process for calculating a relative change ($\Delta S/S_0$) in an imaging scale ($S_0$) for carrying out a computational adaptation of the size of picture elements of a detector for compensating the influence of ambient conditions on an imaging scale (S) in a measuring microscope. FIG. 8 shows a flow diagram of a process for calculating a relative change ($\Delta S/S_0$) in an imaging scale ($S_0$) for carrying out an adjustment of the imaging scale and/or a correction of image positions to the measured for compensating the influence of ambient conditions on an imaging scale (S) in a measuring microscope.

In some implementations, the control and regulating device 15 (FIG. 1) can include one or more processors and one or more computer-readable media (e.g., ROM, DRAM, SRAM, SDRAM, hard disk, optical disk, and flash memory). The one or more processors can perform various computations described above. The computations can also be implemented using application-specific integrated circuits (ASICs). The term "computer-readable medium" refers to a medium that participates in providing instructions to a processor for execution, including without limitation, non-volatile media (e.g., optical or magnetic disks), and volatile media (e.g., memory) and transmission media. Transmission media includes, without limitation, coaxial cables, copper wire, fiber optics and free space. The memory can include any type of memory, such as ROM, DRAM, SRAM, SDRAM, and flash memory.

The features described above can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language (e.g., C, Java), including compiled or interpreted languages, and it can be deployed in any form, including as a stand-alone program or as a module, component, subroutine, a browser-based web application, or other unit suitable for use in a computing environment.

Suitable processors for the execution of a program of instructions include, e.g., general purpose microprocessors, special purpose microprocessors, digital signal processors, single-core or multi-core processors, of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM, DVD-ROM, and Blu-ray BD-ROM disks. The processor and the memory can be supplemented by, or incorporated in, ASICs (application-specific integrated circuits).

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments.

Thus, particular embodiments of the subject matter have been described. Other embodiments are within the scope of the following claims. In some cases, the actions recited in the claims can be performed in a different order and still achieve desirable results.

What is claimed is:

1. A method for capturing the influence of ambient conditions on an imaging scale in a measuring microscope of a mask inspection system or a wafer inspection system,
   wherein a modification of the optical properties in the measuring microscope that is caused by a change in the ambient conditions is measured by use of a reference measurement system,
   wherein the deviation ($\Delta n$) of a refractive index (n) from a reference value ($n_0$) that is caused by changes in the ambient conditions is established in the reference measurement system,
   wherein an image of a reference structure with at least one reference length that is situated on a calibration mask is produced by use of a detector of the measuring microscope,
   wherein a change in the reference length that is caused by the change in the ambient conditions is determined in the image of the reference structure by use of at least one processor in the mask inspection system or the wafer inspection system, and
   wherein a correlation is established between the modification of the optical properties of the reference measurement system and the length change in the image, produced in the detector, of the reference structure of the calibration mask by use of the at least one processor in the mask inspection system or the wafer inspection system.

2. The method as claimed in claim 1, wherein
local changes in a local reference length are determined in the image of the reference structure, and
a local correlation function is established between the modification of the optical properties of the reference measurement system and the local length changes in the image, produced in the detector, of the reference structure of the calibration mask.

3. The method as claimed in claim 1, wherein images of the calibration mask in different positions are produced by use of the detector and changes in the reference length are measured in these images in each case.

4. The method as claimed in claim 3, wherein reference coordinate values ($X_0$, $Y_0$) and associated length changes ($\Delta X$, $\Delta Y$) of the reference coordinate values ($X_0$, $Y_0$) are measured in the images, produced by use of the detector, of the calibration mask.

5. The method as claimed in claim 1, wherein an etalon that is integrated in the measuring microscope is used as the reference measurement system.

6. The method as claimed in claim 1, wherein the correlation between a change in the refractive index ($\Delta n$) and a relative change in the length scale ($\Delta L/L_0$) is used to calculate a relative change ($\Delta S/S_0$) in an imaging scale ($S_0$) of the measuring microscope that is caused by the change in the ambient conditions.

7. The method as claimed in claim 1, wherein the deviation ($\Delta W$) of an optical path ($W$) from a reference value ($W_0$) that is caused by changes in the ambient conditions is established in the reference measurement system.

8. The method as claimed in claim 7, wherein the correlation between a change in the optical path ($\Delta W$) and a relative change in the length scale ($\Delta L/L_0$) is used to calculate a relative change ($\Delta S/S_0$) in an imaging scale ($S_0$) of the measuring microscope that is caused by the change in the ambient conditions.

9. The method as claimed in claim 7, wherein the correlation between a change in the optical path ($\Delta W$) and a relative change in the length scale ($L/L_0$) is a linear correlation.

10. The method as claimed in claim 7, wherein the correlation between a change in the optical path ($\Delta W$) and a relative change in the length scale ($L/L_0$) is a nonlinear correlation.

11. The method as claimed in claim 7, wherein the correlation between a change in the optical path ($\Delta W$) and a relative change in the length scale ($L/L_0$) is established by machine learning.

12. The method of claim 2, comprising producing, using the detector, images of the calibration mask in different positions, and for each image measuring changes ($\Delta L$) in the reference length ($L0$) in the image.

13. The method of claim 2, comprising using an etalon that is integrated in the measuring microscope as a reference measurement system.

14. The method of claim 3, comprising using an etalon that is integrated in the measuring microscope as a reference measurement system.

15. The method of claim 4, comprising using an etalon that is integrated in the measuring microscope as a reference measurement system.

16. The method of claim 2, comprising establishing, in the reference measurement system, the deviation ($\Delta n$) of a refractive index ($n$) from a reference value ($n_0$) that is caused by changes in the ambient conditions.

17. The method of claim 3, comprising establishing, in the reference measurement system, the deviation ($\Delta n$) of a refractive index ($n$) from a reference value ($n_0$) that is caused by changes in the ambient conditions.

18. A method for compensating the influence of ambient conditions on an imaging scale ($S$) in a measuring microscope,
wherein a computational adaptation of the size of picture elements of the detector is carried out on the basis of a relative change ($\Delta S/S_0$) in an imaging scale ($S_0$) that was calculated using a process including:
using a reference measurement system to measure a modification of the optical properties in the measuring microscope that is caused by a change in the ambient conditions,
using a detector of the measuring microscope to produce an image of a reference structure with at least one reference length that is situated on a calibration mask,
determining, using at least one processor, a change in the reference length in the image of the reference structure that is caused by the change in the ambient conditions,
establishing, using the at least one processor, a correlation between the modification of the optical properties of the reference measurement system and the length change in the image, produced in the detector, of the reference structure of the calibration mask,
establishing, in the reference measurement system, the deviation ($\Delta n$) of a refractive index ($n$) from a reference value ($n_0$) that is caused by changes in the ambient conditions, and
calculating the relative change ($\Delta S/S_0$) in the imaging scale ($S_0$) of the measuring microscope that is caused by the change in the ambient conditions using the correlation between a change in the refractive index ($\Delta n$) and a relative change in a length scale ($\Delta L/L_0$).

19. A method for compensating the influence of ambient conditions on an imaging scale ($S$) in a measuring microscope,
wherein an adjustment of the imaging scale and/or a correction of image positions to the measured is carried out on the basis of a relative change ($\Delta S/S_0$) in an imaging scale ($S_0$) that was calculated using a process including:
using a reference measurement system to measure a modification of the optical properties in the measuring microscope that is caused by a change in the ambient conditions,
using a detector of the measuring microscope to produce an image of a reference structure with at least one reference length that is situated on a calibration mask,
determining, using at least one processor, a change in the reference length in the image of the reference structure that is caused by the change in the ambient conditions,
establishing, using the at least one processor, a correlation between the modification of the optical properties of the reference measurement system and the length change in the image, produced in the detector, of the reference structure of the calibration mask, establishing, in the reference measurement system, the deviation ($\Delta n$) of a refractive index (n) from a reference value ($n_0$) that is caused by changes in the ambient conditions, and calculating the relative change ($\Delta S/S_0$) in the imaging scale ($S_0$) of the measuring microscope that is caused by the change in the ambient conditions using the correlation between a change in the refractive index ($\Delta n$) and a relative change in a length scale ($\Delta L/L_0$).

20. A method for capturing the influence of ambient conditions on an imaging scale in a measuring microscope of a mask inspection system or a wafer inspection system, wherein a modification of the optical properties in the measuring microscope that is caused by a change in the ambient conditions is measured by use of a reference measurement system, wherein an image of a reference structure with at least one reference length that is situated on a calibration mask is produced by use of a detector of the measuring microscope, wherein a change in the reference length that is caused by the change in the ambient conditions is determined in the image of the reference structure by use of at least one processor in the mask inspection system or the wafer inspection system, wherein a correlation is established between the modification of the optical properties of the reference measurement system and the length change in the image, produced in the detector, of the reference structure of the calibration mask by use of the at least one processor in the mask inspection system or the wafer inspection system, wherein the deviation ($\Delta W$) of an optical path (W) from a reference value ($W_0$) that is caused by changes in the ambient conditions is established in the reference measurement system, and wherein the correlation between a change in the optical path ($\Delta W$) and a relative change in the length scale ($\Delta L/L_0$) is used to calculate a relative change ($\Delta S/S_0$) in an imaging scale ($S_0$) of the measuring microscope that is caused by the change in the ambient conditions.

21. A method for capturing the influence of ambient conditions on an imaging scale in a measuring microscope of a mask inspection system or a wafer inspection system, wherein a modification of the optical properties in the measuring microscope that is caused by a change in the ambient conditions is measured by use of a reference measurement system, wherein an image of a reference structure with at least one reference length that is situated on a calibration mask is produced by use of a detector of the measuring microscope, wherein a change in the reference length that is caused by the change in the ambient conditions is determined in the image of the reference structure by use of at least one processor in the mask inspection system or the wafer inspection system, wherein a correlation is established between the modification of the optical properties of the reference measurement system and the length change in the image, produced in the detector, of the reference structure of the calibration mask by use of the at least one processor in the mask inspection system or the wafer inspection system, wherein the deviation ($\Delta W$) of an optical path (W) from a reference value ($W_0$) that is caused by changes in the ambient conditions is established in the reference measurement system, and wherein the correlation between a change in the optical path ($\Delta W$) and a relative change in the length scale ($L/L_0$) is a nonlinear correlation.

22. A method for capturing the influence of ambient conditions on an imaging scale in a measuring microscope of a mask inspection system or a wafer inspection system, wherein a modification of the optical properties in the measuring microscope that is caused by a change in the ambient conditions is measured by use of a reference measurement system, wherein an image of a reference structure with at least one reference length that is situated on a calibration mask is produced by use of a detector of the measuring microscope, wherein a change in the reference length that is caused by the change in the ambient conditions is determined in the image of the reference structure by use of at least one processor in the mask inspection system or the wafer inspection system, wherein a correlation is established between the modification of the optical properties of the reference measurement system and the length change in the image, produced in the detector, of the reference structure of the calibration mask by use of the at least one processor in the mask inspection system or the wafer inspection system, wherein the deviation ($\Delta W$) of an optical path (W) from a reference value ($W_0$) that is caused by changes in the ambient conditions is established in the reference measurement system, and wherein the correlation between a change in the optical path ($\Delta W$) and a relative change in the length scale ($L/L_0$) is established by machine learning.

* * * * *